(12) United States Patent
Sagebiel

(10) Patent No.: US 8,844,336 B2
(45) Date of Patent: Sep. 30, 2014

(54) AIR BUBBLE SENSOR

(75) Inventor: Florian Sagebiel, Mettenheim (DE)

(73) Assignee: ZOLL LifeBridge GmbH, Ampfing (DE)

( * ) Notice: Subject to any disclaimer, the term of this patent is extended or adjusted under 35 U.S.C. 154(b) by 638 days.

(21) Appl. No.: 13/052,170

(22) Filed: Mar. 21, 2011

(65) Prior Publication Data

US 2011/0239733 A1   Oct. 6, 2011

(30) Foreign Application Priority Data

Mar. 31, 2010   (EP) ..................................... 10003530

(51) Int. Cl.
| | |
|---|---|
| *G01N 29/02* | (2006.01) |
| *A61M 5/36* | (2006.01) |
| *G01N 29/22* | (2006.01) |
| *A61M 1/36* | (2006.01) |
| *G01N 29/032* | (2006.01) |

(52) U.S. Cl.
CPC ...... *G01N 29/222* (2013.01); *A61M 2205/3375* (2013.01); *G01N 2291/048* (2013.01); *A61M 1/3626* (2013.01); *G01N 29/032* (2013.01); *G01N 2291/02433* (2013.01)
USPC .......................................... 73/19.03; 73/19.1

(58) Field of Classification Search
USPC .............................. 73/19.03, 19.01
See application file for complete search history.

(56) References Cited

U.S. PATENT DOCUMENTS

| | | | | | |
|---|---|---|---|---|---|
| 3,921,622 | A | * | 11/1975 | Cole .............................. | 600/437 |
| 3,974,681 | A | * | 8/1976 | Namery .......................... | 73/600 |
| 4,068,521 | A | * | 1/1978 | Cosentino et al. ........... | 73/19.03 |
| 4,237,720 | A | | 12/1980 | Abts | |
| 5,177,993 | A | | 1/1993 | Beckman et al. | |
| 5,723,773 | A | * | 3/1998 | Bryan .......................... | 73/61.75 |
| 5,811,659 | A | * | 9/1998 | Giebler ........................ | 73/19.03 |
| 6,142,008 | A | | 11/2000 | Cole et al. | |
| 6,231,320 | B1 | | 5/2001 | Lawless et al. | |
| 7,726,174 | B2 | * | 6/2010 | Riley et al. ................... | 73/19.03 |
| 8,033,157 | B2 | * | 10/2011 | Yardimci et al. ............. | 73/19.01 |
| 8,091,442 | B1 | * | 1/2012 | Dam ............................ | 73/866.5 |
| 8,225,639 | B2 | * | 7/2012 | Riley et al. ................... | 73/19.03 |
| 2008/0134750 | A1 | * | 6/2008 | Riley et al. ................... | 73/19.03 |
| 2009/0088687 | A1 | * | 4/2009 | Yardimci et al. ............. | 604/122 |

FOREIGN PATENT DOCUMENTS

| | | |
|---|---|---|
| DE | 692 06 209 T2 | 3/1997 |
| DE | 699 27 263 T2 | 6/2006 |
| EP | 0 524 605 A1 | 1/1993 |
| EP | 0 524 605 B1 | 1/1993 |
| EP | 0 778 465 A1 | 6/1997 |
| EP | 1 085 922 A1 | 3/2001 |
| EP | 1 085 922 B1 | 3/2001 |

OTHER PUBLICATIONS

European Search Report dated Aug. 16, 2010 relating to European Patent Application No. 10 003 530.2.

* cited by examiner

*Primary Examiner* — Lisa Caputo
*Assistant Examiner* — Punam Roy
(74) *Attorney, Agent, or Firm* — Robert D. Buyan; Stout, Uxa & Buyan, LLP

(57) ABSTRACT

An air bubble sensor has a holder at which at least one ultrasonic sensor is arranged to detect air bubbles and/or gas bubbles in a flowing liquid, wherein a flow passage which has connection pieces is integrated into the holder.

55 Claims, 2 Drawing Sheets

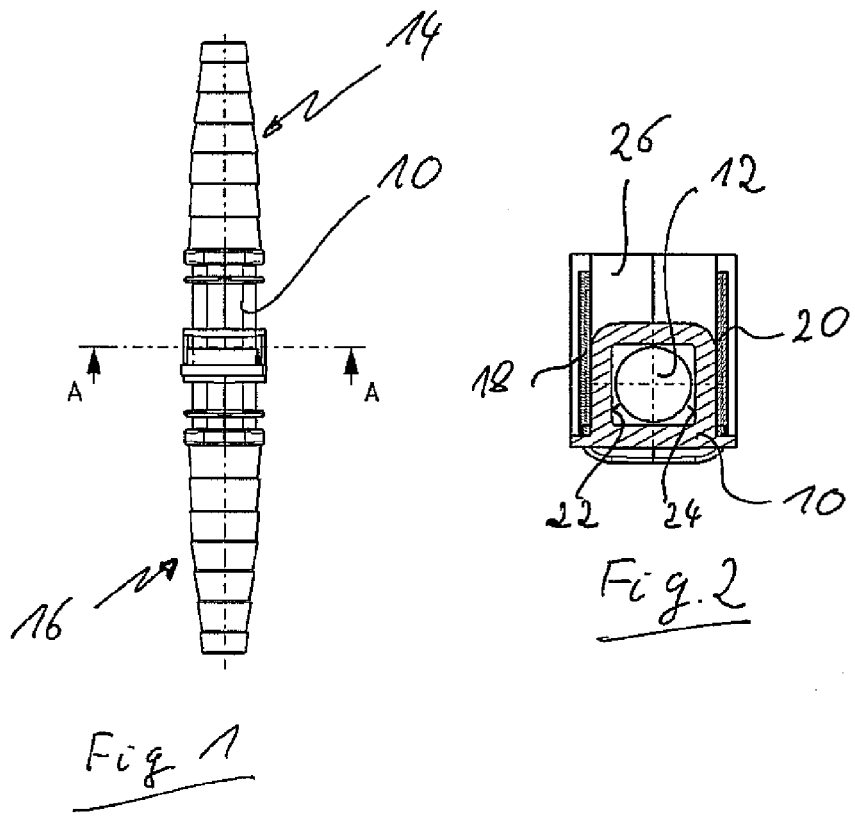
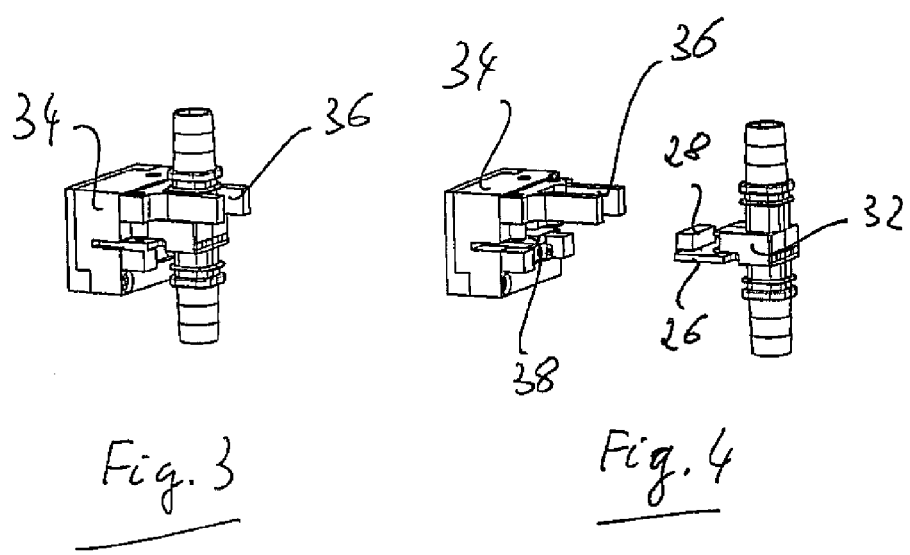

AIR BUBBLE SENSOR

CROSS-REFERENCE TO RELATED APPLICATIONS

This application claims priority of European Patent Application 10003530.2 filed Mar. 31, 2010.

FIELD OF THE INVENTION

The present invention relates to an air bubble sensor having a holder at which at least one ultrasonic sensor is arranged to detect air bubbles and/or gas bubbles in a flowing liquid.

BACKGROUND OF THE INVENTION

Such air bubble sensors are known from practice and serve, for example in mobile heart-lung machines, to increase the safety of the patient from air embolism. As soon as air is detected in a blood conducting tube by such an air bubble sensor, safety clamps can be activated which prevent a further conducting of air bubbles into the patient's body.

In known air bubble sensors, a blood conducting tube is inserted into the holder, which can cost valuable time in an emergency. Air bubble sensors are furthermore known in which a coupling medium has to be introduced into the holder before the insertion of the tube to improve the coupling between the air bubble sensor and the tube. This is in particular likewise time-consuming and prone to error in emergencies.

SUMMARY OF THE INVENTION

It is the object of the present invention to optimize an air bubble sensor of the initially named kind with respect to a use in emergencies. This object is satisfied by the features of the claim and in particular in that a closed flow passage is integrated into the holder, said flow passage having two connection pieces each for a respective tube. Such an air bubble sensor can be connected with the aid of the connection pieces long before use to (then) blood conducting tubes so that, when the air bubble sensor is put into operation, an insertion of a tube or even a provision of a coupling medium is not necessary. By integration of the ultrasonic sensor and of the flow passage as well as the connection pieces into the holder, a single component is provided which can in particular be configured as a disposable part and which can be disposed of after use. The air bubble sensor in accordance with the invention can be manufactured economically and can already be mounted to a mobile heart-lung machine, for example, in production; that is, it is not necessary to carry out assembly steps or adaptation when the system is first put into operation.

Advantageous embodiments of the invention are described in the description, in the drawing and in the dependent claims.

In accordance with a first advantageous embodiment, an ultrasonic sensor element, for example an ultrasonic transmitter and an ultrasonic receiver in the form of piezoceramics, can be arranged, viewed in cross-section, at two sides of the flow passage. The flow passage is hereby easily detected in a manner known per se, with no coupling media, however, having to be provided or repeatedly supplied thanks to the integration of the ultrasonic sensor elements and of the flow passage into a single component. A replacement of gel pads known from the prior art can be dispensed with and the air bubble sensor can be installed at any desired locations without good accessibility for an insertion of a tube being necessary.

In accordance with a further advantageous embodiment, the flow passage can have, at least sectionally, two oppositely disposed wall sections which extend substantially parallel to one another. In this manner, the total flow cross-section can be detected particularly easily with respect to air bubbles since the ultrasound from the—usually parallelepiped shaped—piezoceramics can be easily coupled into the interior of the flow passage.

In accordance with a further advantageous embodiment, the flow passage can—at least sectionally—have a substantially rectangular or square cross-section. Any dead zones within the flow cross-section are hereby precluded and a turbulent flow within the cross-section is avoided.

In accordance with a further advantageous embodiment, the connection pieces can be configured so that tubes having different inner diameters can be pushed onto them. In this manner, the air bubble sensor can be used universally for different tube diameters.

In accordance with a further advantageous embodiment, an electric plug connector for the ultrasonic sensor can be arranged at the holder so that said ultrasonic sensor can be coupled to a device in a particularly simple manner. Electric components to control the ultrasonic sensor can furthermore be arranged at the holder. In this manner, adaptation members and the like, which have to be matched to the sensor elements, can already be adapted during manufacture so that the air bubble sensor subsequently only has to be inserted into an associated device without further settings or adaptation measures being required.

In accordance with a further advantageous embodiment, a plug receiver for the air bubble sensor can be provided which is fastened, for example, to the device with which the air bubble sensor should be used. Such a plug receiver can in particular have a holding clamp for the air bubble sensor so that, on the preassembly, the air bubble sensor only has to be inserted into the holding clamp. After a use of the air bubble sensor, it can be removed from the plug receiver in an extremely simple manner and can, for example, be disposed of.

In accordance with an advantageous embodiment, a cut-out can be provided in the plug receiver and a plug connector of the air bubble sensor is accommodated therein in a protected manner when the air bubble sensor is plugged in. In this manner, an electric contact simultaneously takes place on a plugging of the air bubble sensor into the plug receiver, with the electric plug connector or the electric components of the air bubble sensor being accommodated in the cut-out of the plug receiver in a protected manner.

Furthermore, in accordance with an advantageous embodiment, evaluation electronics for the air bubble sensor can be provided in the plug receiver so that an evaluation of the detected signals can take place without any long electrical lead paths in the region of the plug receiver.

In accordance with an advantageous embodiment, the air bubble sensor has a circuit board with electric or electronic components which engages around the flow passage at two sides. The sensor elements can hereby be arranged on the circuit board so that they are arranged at both sides of the flow passage after pushing the circuit board onto the holder.

It can be advantageous if the holder is configured in one piece and in particular of a material permeable for ultrasound, for example a plastic, since hereby the air bubble sensor can be manufactured particularly economically. Furthermore, the air bubble sensor can be configured as a disposable part; that is the air bubble sensor, the holder and all parts attached thereto can be disposed of after a single use.

In accordance with a further advantageous embodiment of the invention, the flow passage extends in a straight line in the throughflow direction. A turbulent flow is hereby prevented, in particular in the region of the ultrasonic sensor.

BRIEF DESCRIPTION OF THE DRAWINGS

The present invention will be described in the following purely by way of example with reference to an advantageous embodiment and to the enclosed drawings. There are shown:

FIG. 1 is a side view of an air bubble sensor;

FIG. 2 is a section through the air bubble sensor of FIG. 1 along the line A-A;

FIG. 3 is a further embodiment of an air bubble sensor which is inserted into a plug receiver;

FIG. 4 is the air bubble sensor of FIG. 3 before the insertion into the plug receiver.

DETAILED DESCRIPTION OF THE PREFERRED EMBODIMENTS

Figure 5:
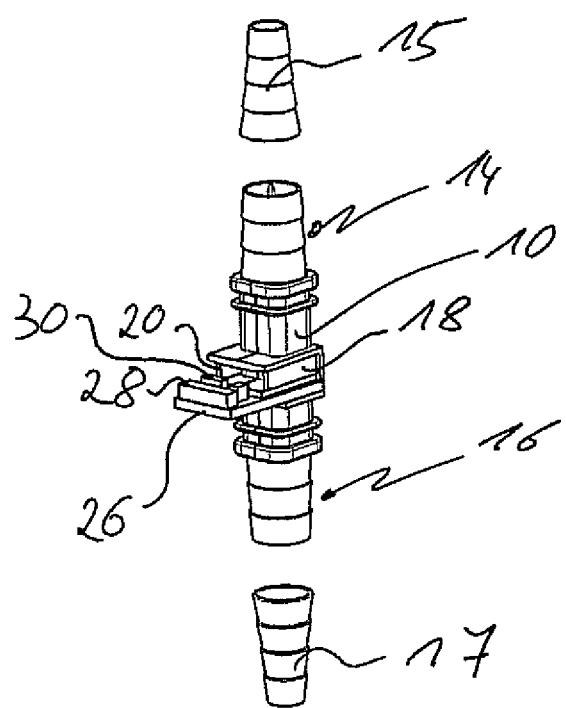
FIG. 5 is a perspective view of the air bubble sensor of FIG. 3 and FIG. 4.

The air bubble sensor shown in FIG. 1 has a holder 10 which is manufactured in one piece from plastic material and in which a flow passage 12 (cf. FIG. 2) is provided which extends in a straight line in the flow direction and which extends from one end of the holder 10 to its other end. The holder 10 has the outer contour of a tube connector and has an upper connection piece 14 and a lower connection piece 16 for one respective tube each. In the embodiment shown, the two connection pieces are configured as conically tapering and screened so that tubes having different inner diameters can be pushed onto the connection pieces. The connection pieces 14 and 16 are divided into individual conical sections having different outer diameters, which facilitates a pushing on of the tubes having different outer diameters.

FIG. 2 shows a section through the air bubble sensor of FIG. 1 along the line A-A, with it being recognizable that a respective ultrasonic sensor element in the form of piezoceramics 18 and 20 is arranged outwardly at the holder 10 at two sides of the flow passage 12, viewed in cross-section. The piezoceramics 18 and 20 have a parallelepiped platelet-shaped structure and are adhesively bonded to the holder which has, in the region of the piezoceramics 18 and 20, two oppositely disposed outer wall sections which extend in parallel to one another and to which the piezoceramics are fastened. In the region of the piezoceramics 18 and 20, that is in the region of the measurement path, the cross-section of the flow passage is configured in square form or approximately square form, whereby an ideal coupling of the ultrasonic waves into the region of the measurement path can take place. As FIG. 2 shows, the ultrasonic sensor elements 18, 20 and the oppositely disposed inner wall sections 22 and 24 of the flow passage 12 extend parallel to one another in the region of the measurement path for this purpose. The cross-section of the flow passage then merges into a round cross-section outside the measurement path.

FIG. 5 shows the air bubble sensor of FIGS. 1 and 2 in a perspective view, wherein outer end sections 15 and 17 have been removed only in the region of the connection pieces 14 and 16. For this purpose, desired break points can, for example, be provided at the end sections 15 and 17 and permit a simple removal.

FIG. 5 illustrates that a circuit board 26 is arranged beneath the ultrasonic sensor elements 18 and 20 on the air bubble sensor and its main surface extends perpendicular to the flow direction. The circuit board 26 engages around the flow passage or the measurement path at two sides so that the ultrasonic sensor elements 18 and 20 can also be fastened to the circuit board 26. A plug connector 28 which enables an electric coupling of the ultrasonic sensor is furthermore located at the front end of the circuit board 26. Electric components such as adaptation elements 30 with which a matching to the ultrasonic sensor elements used can take place are furthermore provided on the circuit board 26.

FIG. 5 illustrates that the air bubble sensor 10, the circuit board 26 as well as the components attached thereto are connected to one another to form a unit which can be handled as such; that is this unit can be preassembled in the factory after its manufacture and can be connected to corresponding tubes. After use, the unit can be unplugged from the tubes and disposed of.

FIGS. 3 and 4 show the air bubble sensor of FIG. 5, wherein a panel 32 is only provided in the region of the sensor elements 18 and 20. FIGS. 3 and 4 furthermore show a plug receiver 34 for the air bubble sensor which has a holding clamp 36 into which the air bubble sensor can be plugged. A cut-out 38 is furthermore provided in the plug receiver 34 and the plug connector 28 as well as the circuit board 26 are accommodated therein in a protected manner with a plugged in air bubble sensor. A complementary plug part is also located within the plug receiver 34 so that not only a mechanical fastening, but also simultaneously an electrical contacting has taken place after insertion of the air bubble sensor into the plug receiver. Evaluation electronics (not shown) for the air bubble sensor are furthermore provided in the plug receiver 34.

The air bubble sensor in accordance with the invention can be integrated directly into a tube system without a coupling to the tube system via a coupling medium having to take place. There is thus no need for the error-prone insertion of a tube and the application of a coupling medium. The air bubble sensor is ready for use directly after the installation and the air bubble sensor can also be positioned at inaccessible points. The sensor can be removed from the plug receiver after utilization and one-time use and can be disposed of with the other tube material. The evaluation electronics can, however, remain in the plug receiver and be utilized again for the following use. The plug receiver can be fastened to the housing of a desired device, for example of a heart-lung machine.

The invention claimed is:

1. An air bubble sensor comprising a holder at which at least one ultrasonic sensor is arranged to detect air bubbles and/or gas bubbles in a flowing liquid and a plug receiver;
   wherein a closed flow passage is integrated into the holder, said closed flow passage having two connection pieces, each connection piece being for a respective tube;
   wherein electric components for controlling the ultrasonic sensor are arranged at the holder;
   wherein evaluation electronics for the air bubble sensor are provided in the plug receiver; and
   wherein the plug receiver has a holding clamp for the air bubble sensor.

2. An air bubble sensor in accordance with claim 1, wherein an ultrasonic sensor element is arranged at two sides of the flow passage viewed in cross-section.

3. An air bubble sensor in accordance with claim 1, wherein at least a portion of the flow passage has two oppositely disposed wall sections which extend substantially parallel to one another.

4. An air bubble sensor in accordance with claim 1, wherein the connection pieces are configured so that tubes having different inner diameters can be pushed onto them.

5. An air bubble sensor in accordance with claim 1, wherein an electric plug connection for the ultrasonic sensor is arranged at the holder.

6. An air bubble sensor in accordance with claim 1, wherein a cut-out is provided in the plug receiver and a plug connector of the air bubble sensor is arranged therein in a protected manner with a plugged-in air bubble sensor.

7. An air bubble sensor in accordance with claim 1 having a circuit board which engages around the flow passage at two sides.

8. An air bubble sensor in accordance with claim 1 having the outer contour of a tube connector.

9. An air bubble sensor in accordance with claim 1, wherein the holder is configured in one piece and is permeable by ultrasound.

10. An air bubble sensor in accordance with claim 1 being configured as a disposable part.

11. An air bubble sensor in accordance with claim 1, wherein the flow passage extends in a straight line in the throughflow direction.

12. An air bubble sensor according to claim 1 wherein at least a portion of the flow passage has a substantially rectangular or square cross-section.

13. An air bubble sensor comprising:
a holder at which at least one ultrasonic sensor is arranged to detect air bubbles and/or gas bubbles in a flowing liquid;
a closed flow passage integrated into the holder, said closed flow passage having two connection pieces, each connection piece being for a respective tube; and
a circuit board which engages around the flow passage at two sides;
wherein the plug receiver has a holding clamp for the air bubble sensor.

14. An air bubble sensor in accordance with claim 13, wherein an ultrasonic sensor element is arranged at two sides of the flow passage viewed in cross-section.

15. An air bubble sensor in accordance with claim 13, wherein at least a portion of the flow passage has two oppositely disposed wall sections which extend substantially parallel to one another.

16. An air bubble sensor in accordance with claim 13, wherein the connection pieces are configured so that tubes having different inner diameters can be pushed onto them.

17. An air bubble sensor in accordance with claim 13, wherein an electric plug connection for the ultrasonic sensor is arranged at the holder.

18. An air bubble sensor in accordance with claim 13 wherein electric components for controlling the ultrasonic sensor are arranged at the holder.

19. An air bubble sensor in accordance with claim 13, wherein a cut-out is provided in the plug receiver and a plug connector of the air bubble sensor is arranged therein in a protected manner with a plugged-in air bubble sensor.

20. An air bubble sensor in accordance with claim 13 wherein evaluation electronics for the air bubble sensor are provided in the plug receiver.

21. An air bubble sensor in accordance with claim 13 having the outer contour of a tube connector.

22. An air bubble sensor in accordance with claim 13, wherein the holder is configured in one piece and is permeable by ultrasound.

23. An air bubble sensor in accordance with claim 13 being configured as a disposable part.

24. An air bubble sensor in accordance with claim 13, wherein the flow passage extends in a straight line in the throughflow direction.

25. An air bubble sensor comprising a holder at which at least one ultrasonic sensor is arranged to detect air bubbles and/or gas bubbles in a flowing liquid and a plug receiver;
wherein a closed flow passage is integrated into the holder, said closed flow passage having two connection pieces, each connection piece being for a respective tube;
wherein electric components for controlling the ultrasonic sensor are arranged at the holder;
wherein evaluation electronics for the air bubble sensor are provided in the plug receiver; and
wherein the holder is configured in one piece and in particular from a material permeable for ultrasound.

26. An air bubble sensor in accordance with claim 25, wherein an ultrasonic sensor element is arranged at two sides of the flow passage viewed in cross:-section.

27. An air bubble sensor in accordance with claim 25, wherein at least a portion of the flow passage has two oppositely disposed wall sections which extend substantially parallel to one another.

28. An air bubble sensor in accordance with claim 25, wherein the connection pieces are configured so that tubes having different inner diameters can be pushed onto them.

29. An air bubble sensor in accordance with claim 25, wherein an electric plug connection for the ultrasonic sensor is arranged at the holder.

30. An air bubble sensor in accordance with claim 25, wherein a cut-out is provided in the plug receiver and a plug connector of the air bubble sensor is arranged therein in a protected manner with a plugged-in air bubble sensor.

31. An air bubble sensor in accordance with claim 25 having a circuit board which engages around the flow passage at two sides.

32. An air bubble sensor in accordance claim 25, wherein it has the outer contour of a tube connector.

33. An air bubble sensor in accordance with claim 25, wherein it is configured as a disposable part.

34. An air bubble sensor in accordance with claim 25, wherein the flow passage extends in a straight line in the throughflow direction.

35. An air bubble sensor according to claim 25 wherein at least a portion of the flow passage has a substantially rectangular or square cross-section.

36. An air bubble sensor comprising a holder at which at least one ultrasonic sensor is arranged to detect air bubbles and/or gas bubbles in a flowing liquid and a plug receiver;
wherein a closed flow passage is integrated into the holder, said closed flow passage having two connection pieces, each connection piece being for a respective tube;
wherein electric components for controlling the ultrasonic sensor are arranged at the holder;
wherein evaluation electronics for the air bubble sensor are provided in the plug receiver; and
wherein at least a portion of the flow passage has a substantially rectangular or square cross-section.

37. An air bubble sensor in accordance with claim 36 wherein the holder is configured in one piece and in particular from a material permeable for ultrasound.

38. An air bubble sensor in accordance with claim 36, wherein an ultrasonic sensor element is arranged at two sides of the flow passage viewed in cross:-section.

39. An air bubble sensor in accordance with claim 36, wherein at least a portion of the flow passage has two oppositely disposed wall sections which extend substantially parallel to one another.

40. An air bubble sensor in accordance with claim 36, wherein the connection pieces are configured so that tubes having different inner diameters can be pushed onto them.

41. An air bubble sensor in accordance with claim 36, wherein an electric plug connection for the ultrasonic sensor is arranged at the holder.

42. An air bubble sensor in accordance with claim 36, wherein a cut-out is provided in the plug receiver and a plug connector of the air bubble sensor is arranged therein in a protected manner with a plugged-in air bubble sensor.

43. An air bubble sensor in accordance with claim 36 having a circuit board which engages around the flow passage at two sides.

44. An air bubble sensor in accordance claim 36, wherein it has the outer contour of a tube connector.

45. An air bubble sensor in accordance with claim 36, wherein it is configured as a disposable part.

46. An air bubble sensor in accordance with claim 36, wherein the flow passage extends in a straight line in the throughflow direction.

47. An air bubble sensor comprising:
- a holder at which at least one ultrasonic sensor is arranged to detect air bubbles and/or gas bubbles in a flowing liquid;
- a closed flow passage integrated into the holder, said closed flow passage having two connection pieces, each connection piece being for a respective tube; and
- a circuit board which engages around the flow passage at two sides;
- wherein the holder is configured in one piece and in particular from a material permeable for ultrasound.

48. An air bubble sensor in accordance with claim 47, wherein at least a portion of the flow passage has two oppositely disposed wall sections which extend substantially parallel to one another.

49. An air bubble sensor in accordance with claim 47, wherein the connection pieces are configured so that tubes having different inner diameters can be pushed onto them.

50. An air bubble sensor in accordance with claim 47, wherein an electric plug connection for the ultrasonic sensor is arranged at the holder.

51. An air bubble sensor in accordance with claim 47 wherein electric components for controlling the ultrasonic sensor are arranged at the holder.

52. An air bubble sensor in accordance with claim 47, wherein a cut-out is provided in the plug receiver and a plug connector of the air bubble sensor is arranged therein in a protected manner with a plugged-in air bubble sensor.

53. An air bubble sensor in accordance with claim 47 wherein evaluation electronics for the air bubble sensor are provided in the plug receiver.

54. An air bubble sensor in accordance claim 47 having the outer contour of a tube connector.

55. An air bubble sensor in accordance with claim 47, wherein an ultrasonic sensor element is arranged at two sides of the flow passage viewed in cross-section.

\* \* \* \* \*